US006368266B1

(12) United States Patent
deBeer

(10) Patent No.: US 6,368,266 B1
(45) Date of Patent: Apr. 9, 2002

(54) MEDICAL IRRADIATION ASSEMBLY AND METHOD

(75) Inventor: Nicholas C. deBeer, San Francisco, CA (US)

(73) Assignee: Vascular Architects, Inc., San Jose, CA (US)

( * ) Notice: Subject to any disclaimer, the term of this patent is extended or adjusted under 35 U.S.C. 154(b) by 0 days.

(21) Appl. No.: 09/439,069

(22) Filed: Nov. 12, 1999

(51) Int. Cl.[7] .................................................. A61N 5/00
(52) U.S. Cl. ............................................................ 600/3
(58) Field of Search .......................................... 600/1–8

(56) References Cited

U.S. PATENT DOCUMENTS

| | | | |
|---|---|---|---|
| 5,213,561 A | 5/1993 | Weinstein et al. ............. | 600/7 |
| 5,302,168 A | 4/1994 | Hess .............................. | 600/3 |
| 5,484,384 A | 1/1996 | Fearnot ......................... | 600/3 |
| 5,498,227 A | 3/1996 | Mawad .......................... | 600/3 |
| 5,730,698 A | 3/1998 | Fischell et al. ................ | 600/3 |
| 5,782,742 A | 7/1998 | Crocker et al. ................ | 600/3 |
| 5,840,008 A | 11/1998 | Klein et al. .................... | 600/3 |
| 5,840,009 A | 11/1998 | Fischell et al. ................ | 600/3 |
| 5,843,163 A | 12/1998 | Wall .............................. | 623/1 |
| 5,863,285 A | 1/1999 | Coletti .......................... | 600/3 |
| 5,865,720 A * | 2/1999 | Hastings et al. ............... | 600/3 |
| 5,871,437 A | 2/1999 | Alt ................................. | 600/3 |
| 6,149,574 A * | 11/2000 | Trauthen et al. ............... | 600/3 |
| 6,159,140 A * | 12/2000 | Loeffler et al. ................ | 600/3 |
| 6,183,410 B1 * | 2/2001 | Jacobsen et al. .............. | 600/3 |
| 6,200,256 B1 * | 3/2001 | Weinberger .................... | 600/3 |

FOREIGN PATENT DOCUMENTS

| | | | |
|---|---|---|---|
| WO | WO99/29370 | 6/1999 | ............ A61N/5/00 |
| WO | WO99/40971 | 8/1999 | ............ A61N/5/10 |
| WO | WO99/40972 | 8/1999 | ............ A61N/5/10 |
| WO | WO99/40973 | 8/1999 | ............ A61N/5/10 |
| WO | WO99/40974 | 8/1999 | ............ A61N/5/10 |
| WO | WO99/42167 | 8/1999 | |

OTHER PUBLICATIONS

Hall et al.., "Chapter 7—The Basic Radiobiology of Intravascular Irradiation," R. Waksman (ed.), *Vascular Brachytherapy, Second Edition*, Armonk, NY, Futura Publishing Co., Inc., ©1999, pp. 63–72.

* cited by examiner

Primary Examiner—John P. Lacyk
Assistant Examiner—Joseph A.. Cadugan
(74) Attorney, Agent, or Firm—James F. Hann; Haynes Beffel & Wolfeld LLP

(57) ABSTRACT

A medical irradiation assembly (2) and method provides the target tissue (34) of a vessel (36) with a controlled dose of radiation in a simple, safe and effective manner. A catheter shaft (8) has a balloon (22) at its distal end (20) and a continuous loop, circumferentially-extending radiation source (32) configured to be expansible within the balloon and to be axially translated along and in contact with the inside surface (38) of the balloon by a pull wire (16). Proximal and distal radiation shields (18, 30) are used to house the radiation source, which may be a β source, before and after use. The continuous-loop radiation source stays in contact with the inside surface of the balloon so that the radiation source remains a constant distance, typically the thickness of the balloon, from the target tissue and irradiates the target tissue uniformly.

6 Claims, 3 Drawing Sheets

FIG. 6A

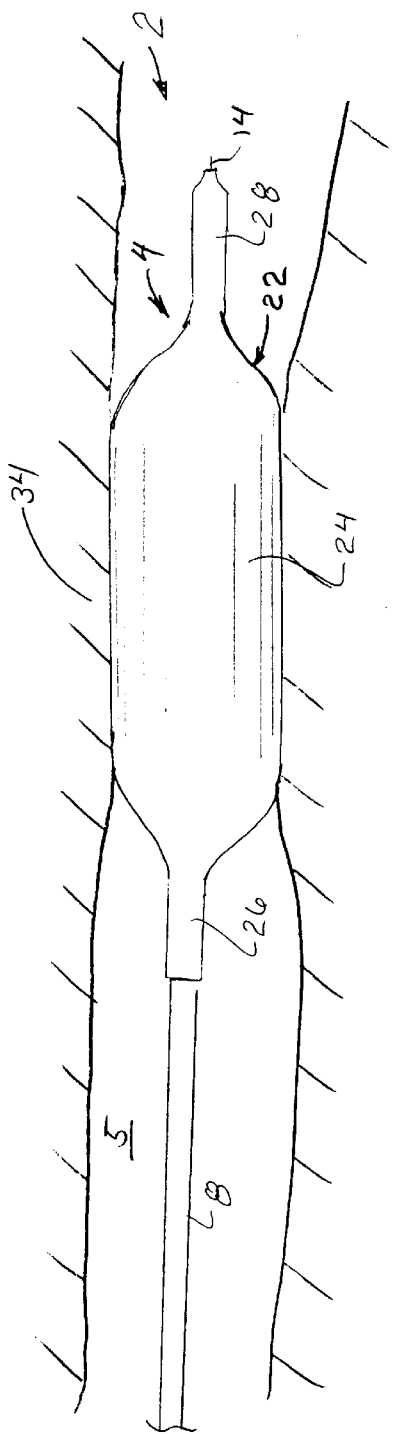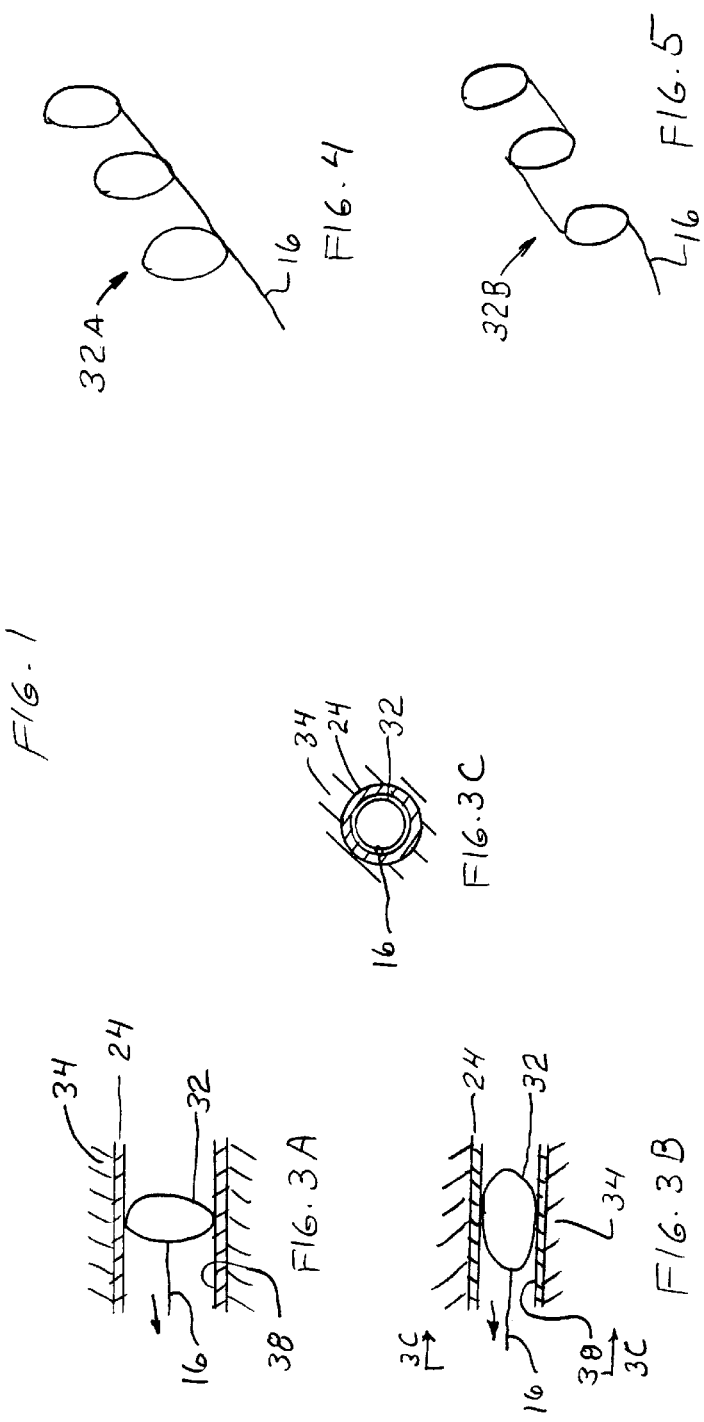

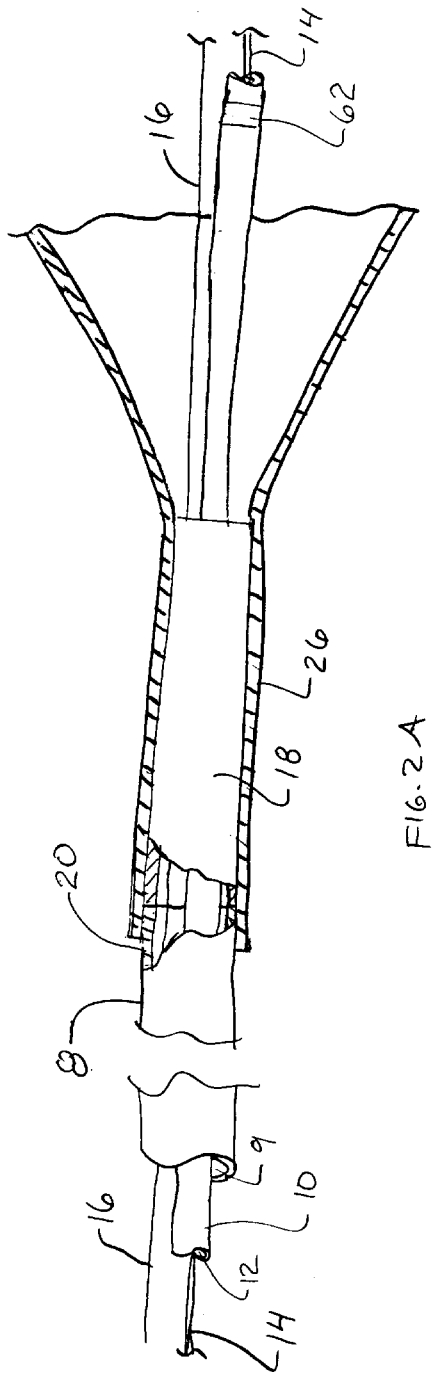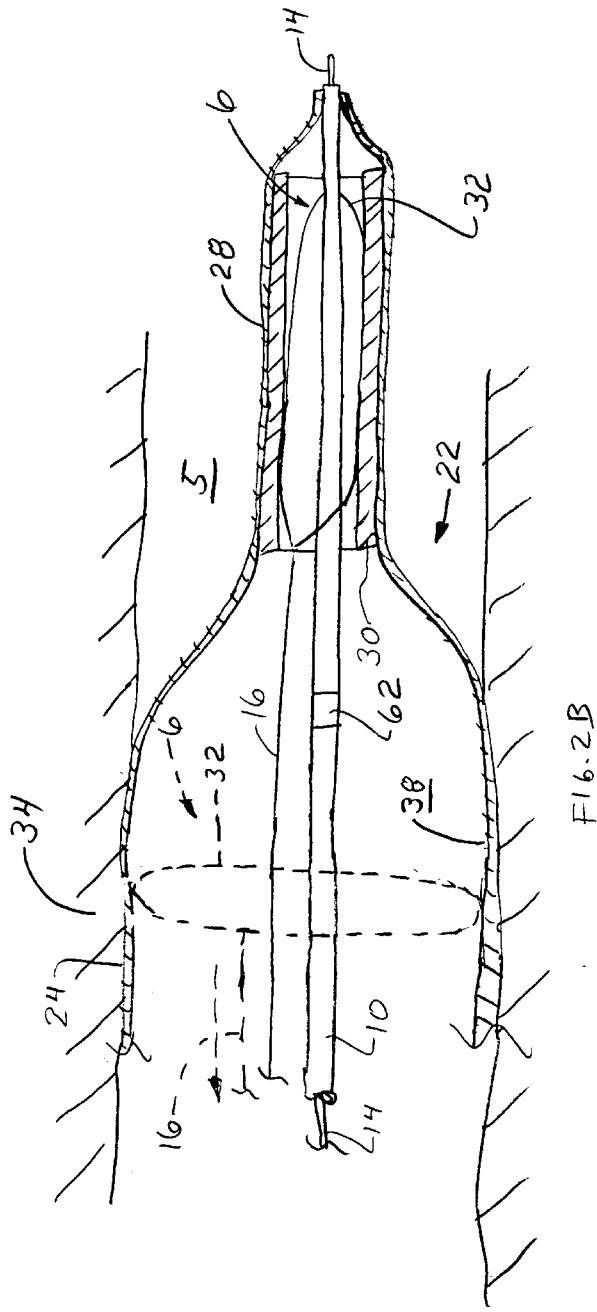

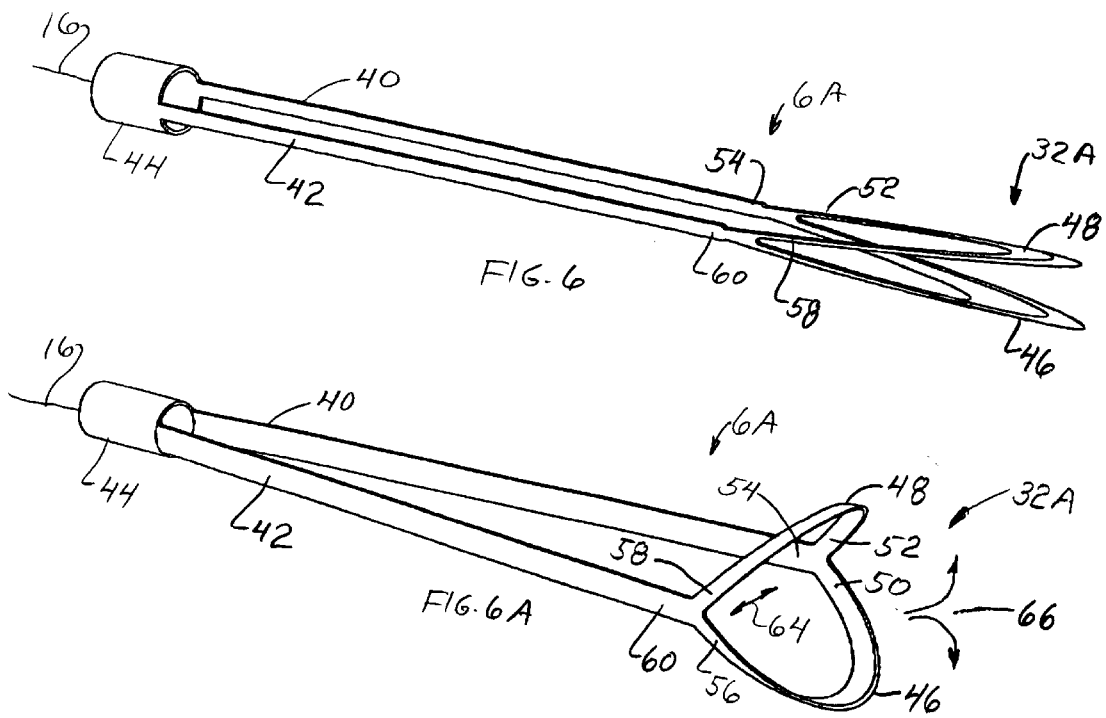
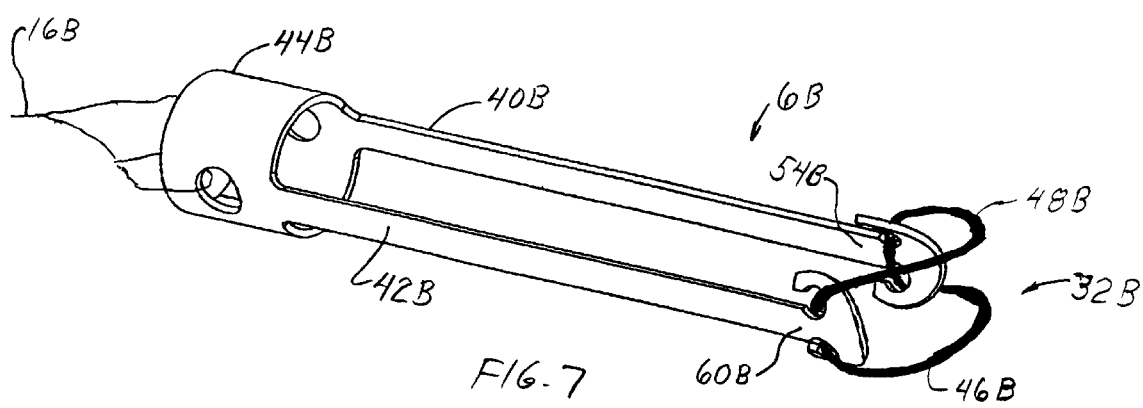

MEDICAL IRRADIATION ASSEMBLY AND METHOD

BACKGROUND OF THE INVENTION

Occlusion of coronary arteries can proceed to the point where a myocardial infarction, that is a heart attack, occurs. Various procedures and therapies are used to reduce or eliminate blockages within the coronary vessels. One method used to treat vascular vessels is angioplasty, in which an expansible element, typically a balloon, is passed through the vessel to the target site and expanded to dilate the vessel and thus restore adequate blood flow through the vessel. One of the problems with angioplasty is that it is subject to restenosis, that is the renarrowing of the vessel after the vessel has been widened by the angioplasty procedure. Various ways have been used to help prevent this restenosis, including athrectomy, stenting, laser techniques, and the use of various pharmacological compositions including calcium antagonists, ace inhibitors, fish oils and steroids.

Another approach used to help prevent restenosis is through irradiation of the target site. This approach is described in, for example, U.S. Patent Nos. 5,484,384 and 5,840,008. One of the keys to radiation therapy is the controlled, typically uniform, irradiation of the target tissue. It is undesirable to provide too much or too little radiation to all or parts of the target site. Other problems associated with irradiating vessels include shielding the radiation source when not being used to actively irradiate the target site, and ensuring the safety of the medical personnel before, during and after the radiation procedure.

SUMMARY OF THE INVENTION

The present invention is directed to a medical irradiation assembly and method which ensures that the target site within a vessel is provided with a uniform, controlled dose of radiation in a simple, safe and effective manner.

A first aspect of the invention is directed to a catheter having an expansible membrane near its distal end and a continuous loop, circumferentially-extending radiation source configured to be expansible within the expansible membrane and to be axially translated along and in contact with the inner surface of the expansible membrane. The expansible membrane is typically a balloon. The radiation source may be mounted to an elongate manipulator. The expansible radiation source may be self-expanding or may be selectively expansible. The expansible radiation source may be, for example, a single radioactive loop.

Another aspect of the invention is directed to a medical irradiation assembly including a balloon catheter having an inflatable balloon with an inside surface, a continuous loop, circumferentially-extending radiation source placeable along a circumferential path against the inside surface of the balloon when the balloon is inflated, and a manipulator for moving the radiation source through the balloon while maintaining contact with the balloon. One or more radiation shields may be used to house the radiation source, preferably a β source, when not in use.

A further aspect of the invention is directed to a method for delivering a radiation dose to a body lumen by expanding a membrane against a wall of the body lumen and passing a continuous loop, circumferentially-extending radiation source along and in contact with the inner surface of the membrane so that radiation passes into the wall of the lumen. The radiation source may be shielded before and after it is passed along the inner surface of the membrane.

A still further aspect of the invention is directed to a kit including an expansible membrane, an irradiation source and instructions for use as discussed above.

With the present invention the continuous-loop radiation source can be made to stay in contact with the membrane. This ensures (1) that the radiation source remains a constant distance, the thickness of the membrane in a preferred embodiment, from the target tissue, and (2) that there are no gaps as exist between conventional discrete, spaced-apart radiation sources; as a result, the target tissue can be irradiated uniformly. This is important when the effectiveness of the irradiation is very sensitive to distance from the target tissue, as it is with many β radiation sources.

Another advantage of the present invention is that it enables the effective shielding of the radiation source before and after the actual procedure. Also, effective shielding is aided by using a β source as the radiation source.

Other features and advantages of the invention will appear from the following description in which the preferred embodiments have been set forth in detail in conjunction with the accompanying drawings.

BRIEF DESCRIPTION OF THE DRAWINGS

FIG. 1 is an overall view of a medical irradiation assembly, shown without its proximal end adapter, within a vessel with the balloon in an inflated condition;

FIGS. 2A and 2B are enlarged partial cross-sectional views of the proximal and distal portions of the balloon of FIG. 1 with a radiation loop housed within a distal radiation shield and showing the radiation loop and pull wire in dashed lines being pulled through the balloon;

FIG. 3A is a simplified side view illustrating the radiation loop of FIG. 2 passing through a slightly smaller diameter lumen than in FIG. 2;

FIG. 3B is similar to that of FIG. 3A but with the radiation loop passing through a still smaller diameter lumen causing the radiation loop to become more elongated;

FIG. 3C is a cross-sectional view taken along line 3C—3C of FIG. 3B showing how at least substantially all of the radiation loop remains in contact with the inside surface of the balloon; FIGS. 4 and 5 illustrate two alternative embodiments of the radiation loop of FIGS. 1–3C;

FIG. 6 illustrates an alternative embodiment of the radiation assembly of FIGS. 1 and 2 with the radiation loop in a radially contracted condition; and FIG. 6A illustrates the radiation assembly of FIG. 6 with the radiation loop in a radially-expanded condition and;

FIG. 7 illustrates a further alternative embodiment of the radiation assembly of FIGS. 6 and 6A.

DESCRIPTION OF THE SPECIFIC EMBODIMENTS

FIGS. 1, 2A and 2B illustrate a medical irradiation assembly 2 made according to the invention. Assembly 2 includes broadly a balloon catheter 4, shown within a blood vessel lumen 5 in FIG. 1, housing a radiation assembly 6, shown in FIG. 2B. Balloon catheter 4 includes a catheter shaft 8 having a central lumen 9 which houses a hollow guidewire shaft 10 defining a guidewire lumen 12. Guidewire lumen 12 houses a conventional guidewire 14 while central lumen 9 houses a pull wire 16. Pull wire 16 may be made from, for example, stainless steel, titanium or nitinol with a diameter of about .13 mm (.005 in) to 1.3 mm (.050 in). A tubular, proximal radiation shield 18 made of, for example, gold, tantalum, tungsten or platinum, butts against the distal end 20 of catheter shaft 8, the purpose of shield 18 being discussed below. Balloon catheter 4 also includes a balloon 22 having a main portion 24, shown inflated in FIGS. 1, 2A and 2B, and proximal and distal sleeve portions 26, 28 surrounding and secured to proximal radiation shield 18 and a tubular distal radiation shield 30. Main portion 24 of balloon 22 is shown in FIGS. 1 and 2B contacting target tissue 34. Main portion 24 of balloon 22 is shown to have a substantially constant diameter. Balloon 22 could be made to have a varying diameter or a varying cross-sectional shape, or both, if desired. Also, balloon 22 can be made from compliant or noncompliant material; that is, balloon 22 may be made from material which is flexible and elastic or flexible and inelastic.

Radiation assembly 6 includes broadly pull wire 16, which acts as a manipulator, and a shape memory radiation loop 32. Radiation loop 32 is preferably made of a shape memory material which naturally expands to a continuous loop, preferably a circular loop oriented perpendicularly to pull wire 16. Radiation loop 32 is preferably of a self-expanding material, such as a nickel titanium alloy; radiation loop 32 could also be made so to be selectively expansible, such as by mechanical actuation or by heating. In one preferred embodiment pull wire 16 and loop 32 are made from round wire having a 0.25 mm (.01 in) diameter and made of nickel titanium alloy shaped with heat and laser welded to close the end of the loop. Radiation loop 32 is, by definition, radioactive; the entire loop 32 may be radioactive or radioactivity may be provided as a coating, segment, strip or otherwise. However, it is desired that radiation loop 32 be made radioactive in a manner such that radiation emitted by the loop will provide substantially uniform irradiation to the target tissue 34 surrounding the inflated balloon 22. Depending on the particular shape of radiation loop 32 and upon the desired pattern of irradiation, the radioactive material may or may not be applied uniformly over the radiation loop.

FIG. 2B illustrates radiation loop 32 housed within distal radiation shield 30, as it would be prior to use. During use the operator pulls on pull wire 16 causing radiation loop 32 to be removed from distal radiation shield 30 and enter into main portion 24 of balloon 22. This is indicated in dashed lines in FIG. 2B. When so disposed, radiation loop 32 automatically tends to assume its radially-expanded condition with loop 32 generally perpendicular to pull wire 16. This helps ensure loop 32 contacts the inside surface 38 of balloon 22 over the entire length of loop 32. Pull wire 16 is preferably moved at a controlled, typically constant, rate so to ensure that radiation from radiation loop 32, which passes through balloon 22 and into target tissue 34, does so at a desired rate. While it may be possible to manually pull pull wire 16 at a constant rate, it is likely that some type of motorized pullback device which pulls pull wire 16 at a constant, or other preprogrammed, rate will be used. Once radiation loop 32 is fully housed within proximal radiation shield 18, the proximal movement of pull wire 16 is halted. Appropriate locking devices or mechanisms may be used to prevent pull wire 16 from being used to pull radiation loop 32 into central lumen 9 and to prevent pull wire 16 from being used to push radiation loop 32 out of proximal radiation shield 18 and into balloon 22. This provides several advantages, including the prevention of undesired irradiation of a patient or medical personnel and the improper use of medical irradiation assembly 2 when constructed to be a single use item.

FIG. 2B illustrates the situation in which radiation loop 32 in its fully radially-expanded condition has a diameter approximately equal to the diameter of lumen 5 at target tissue 34. However, radiation loop 32 accommodates different size lumens and lumens which vary in size over their lengths. For example, FIGS. 3A and 3B illustrate, in schematic form, pull wire 16 pulling radiation loop 32 through an intermediate diameter lumen (FIG. 3A) and through a somewhat narrower diameter lumen (FIG. 3B). This narrowing of the diameter of the lumen is accommodated by radiation loop 32 becoming more oval. However, as shown in FIG. 3C, radiation loop 32 maintains contact with the inside surface 38 of balloon 22, even when deformed, as the loop is moved along inside surface 38. This tendency to remain in contact with inside surface 38 is primarily due to the shape of loop 32, the resilient, shape memory aspects of the material from which loop 32 is made and the fact that the connection between loop 32 and pull wire 16 has a strong tendency to maintain loop 32 and pull wire 16 at 90 degrees to one another.

Instead of single radiation loop 32, multiple radiation loops 32A, 32B, shown in FIGS. 4 and 5, could also be used. The speed of travel of radiation loop 32 may also be varied according to the diameter of lumen 36 to help ensure that the desired amount of radiation is received at the proper locations within lumen 36.

FIGS. 6 and 6A illustrate the distal ends of an alternative embodiment of a radiation assembly made according to the invention with like reference numerals referring to like elements. Radiation assembly 6A includes a pull wire 16, only the distal most end of which is shown in FIGS. 6 and 6A, and a radiation loop 32A, secured to pull wire 16 by a pair of flexible arms 40, 42 extending from a sleeve 44. In the disclosed embodiment sleeve 44, arms 40, 42 and loop 32A are all cut from a single tubular member and the desired continuous-loop shape (see FIG. 6A) is imparted to the first and second segments 46, 48 of loop 32A. Segments 46, 48 have first ends 50, 52 secured to and extending from the distal end 54 of arm 40 and second ends 56, 58 extending from the distal end 60 of arm 42. When in a radially contracted state within a radiation shield, see FIG. 6, arms 40, 42 are generally parallel to one another with segments 46, 48 forming narrow, generally V-shaped configurations. When allowed to open to an expanded configuration, a natural bias of radiation loop 32A causes distal ends 54, 60 to separate and segments 46, 48 to pivot outwardly as indicated by arrows 64, 66. The entire length of radiation loop 32A will thus be biased against inside surface 38 of balloon 22, thus maintaining loop 32A in full or effectively full contact with the inside surface, thus ensuring the desired close and proper spacing between radiation loop 32 and target tissue 34.

FIG. 7 illustrates an alternative embodiment of the radiation assembly of FIGS. 6 and 6A with like reference numerals referring to like elements. In particular loop 32B is formed from radioactive, shape memory metal wire wound to form the first and second segments 46B, 48B of radiation loop 32B.

Remote visualization of the various components of assembly 2 can be aided by locating radiation shields 18, 28, which are radiopaque, and by the use of radiopaque markers 62 on guidewire 14. Radiation loop 32 will also typically be remotely visualizable.

Medical studies (see *Vascular Brachvtherapy*, 2Ed., Chapters 21 & 36, Futura Publishing Co., 1999) have shown that radiation of 18 gray to a 2 mm depth is necessary or desirable to achieve the desired therapeutic result, in particular prohibiting restenosis by damaging cells. That is, the radiation level does not kill the cells but substantially inhibits their replication so to delay or possibly prevent restenosis. While both gamma and beta radiation can be used to provide the desired therapeutic results, that is the inhibition of neointimal hyperplasia, gamma radiation has high penetration powers, capable of penetrating several centimeters of lead. Beta radiation can penetrate, for example, only a few millimeters of aluminum a few centimeters of some plastics. Thus, a radiation shield incorporated into the catheter for a beta radiation source is practical, while one for a gamma radiation source may not be. Therefore, beta radiation sources may be preferred because it allows one to use the radiation source in existing facilities. However, beta sources are very sensitive to distance. This is accommodated by the present invention because the radiation source is maintained in contact with the inside surface of the balloon.

Radioactive sources include radioactive materials or radioisotopes emitting gamma ($\gamma$) and beta ($\beta$) radiation and sometimes a combination of both. Exemplary radioisotopes include $^{192}$Iridium (half life of 74.2 days) emitting a spectrum of $\gamma$ plus $\beta$ radiation, $^{125}$Iodine (half life of 59.6 days) emitting radiation, $^{90}$Strontium (half life of 28.1 years) and $^{90}$Yttrium (half life of 64.1 hours), both emitting $\beta$ radiation only. $^{90}$Strontium, which decays to $^{90}$Yttrium, may be a particularly attractive radioactive source in that both isotopes together, when reaching equilibrium, will emit radiation on a 1 to 1 activity basis, with the $^{90}$Strontium emitting low energy radiation (maximum of 0.54 Mev) and the $^{90}$Yttrium emitting high energy radiation (maximum of 2.27 Mev). As the short lived $^{90}$Yttrium decays to $^{90}$Zirconium, it is replenished by the decay of the long lived $^{90}$Strontium. $^{32}$Phosphorous, which emits $\beta$ and has a half-life of 14.29 days, may also be considered. X-ray radiation sources may also be used. Radiation sources having longer half-lives, on the order of years, have a shelf life which is much longer than radiation sources having a half-life measured in hours or days. However, radiation sources having shorter half-lives can create fewer disposal problems. The choice of the particular radioisotope(s) chosen will depend on several factors including half-life, operating environment, radiation levels needed and disposal constraints.

By maintaining the radiation source so it slides along the inside surface of the balloon, and by controlling the speed at which the radiation source is pulled through the balloon, controlled radiation of the tissue is achieved. The present invention is designed so that irradiation can be done relatively quickly in a conventional operating room without the need for anyone in the room to have individual radiation shielding.

In use, medical irradiation assembly 2 is typically introduced into lumen 5 of a blood vessel through an introducer sheath, not shown, until balloon 22 is aligned with target tissue 34, typically aided by the remote visualization of radiation shields 18, 28 and radiopaque markers 62. Balloon 22 is then inflated to the inflated condition of FIG. 2 and pull wire 16 is pulled proximally in a controlled manner, typically using some type of automated pullback device. Radiation loop 32 is typically pulled at a speed of about 0.5 to 20 cm/min. Upon reaching the end of the zone to be irradiated, radiation loop 32 is pulled into proximal radiation shield 18 where appropriate latching mechanisms prevent it from being pulled proximally or pushed distally from proximal radiation shield 18. Other procedures, such as angioplasty or drug delivery, may be conducted using assembly 2. Upon deflation of balloon 22, assembly 2 is removed from the patient.

Modification and variation can be made to the disclosed embodiments without departing from the subject of the invention as defined in the following claims. For example, balloon 22 could be configured so that when expanded, one edge of the balloon is generally aligned with pull wire 16 at one edge of catheter shaft 8; this would help to keep pull wire 16 at or near inside surface 38 of balloon 22 and thus help to keep that portion of radiation loop 32 adjacent to the pull wire in contact with inside surface 38 of the balloon. Pull wire 16 and/or loop 32 could have cross-sectional shapes other than round, such as flattened. A flattened cross-sectioned pullwire 16 preferably has a maximum width of about 2 mm.

Any and all patents, applications and printed publications referred to above are incorporated by reference.

What is claimed is:

1. A system for delivering a radioactive dose to a body lumen, said system comprising:
    a catheter comprising a catheter body, having a proximal end and a distal end, and an inflatable balloon at the distal end of the catheter body;
    a manipulator comprising first and second elongate members having respective first and second distal ends; and
    an expansible radiation source configured to be expansible within the inflatable balloon and to be axially translated along and in contact with an inner surface of the inflatable balloon, the expansible radiation source comprising first and second elongate radioactive elements each having first and second proximal ends, the first proximal ends of the first and second radioactive elements extending from the first distal end of the first elongate member, the second proximal ends of the first and second radioactive elements extending from the second distal end of the second elongate member, the radioactive elements tending to expand from a radially contracted state to generally U-shaped elements in a radially expanded state.

2. A system as in claim 1, wherein the manipulator has a width which does not exceed 2mm.

3. A system as in claim 1, wherein the expansible radiation source is resilient so that it may be radially constrained at a narrow profile and released to self-expand to a larger profile.

4. A system as in claim 1, wherein the expansible radiation source comprises means for selective expansion of said radiation source.

5. A system as in claim 1 further comprising a radiation shield carried by the catheter and configured to house the radiation source when not in use.

6. A system as in claim 1 wherein the radiation source is a beta source.

* * * * *